United States Patent
Nair et al.

(10) Patent No.: US 10,308,970 B2
(45) Date of Patent: *Jun. 4, 2019

(54) METHODS FOR CONTROLLING FUCOSYLATION LEVELS IN PROTEINS

(71) Applicant: BIOCON LIMITED, Bangalore (IN)

(72) Inventors: Pradip Nair, Bangalore (IN); Ramakrishnan Melarkode, Bangalore (IN); Rasika Venkataraman, Bangalore (IN); Laxmi Adhikary, Bangalore (IN); Ankur Bhatnagar, Bangalore (IN); Sunaina Prabhu, Sirsi (IN); Kriti Shukla, Ahmedabad (IN); Dinesh Baskar, Bangalore (IN); Saravanan Desan, Bangalore (IN); Harish Venkatraman Pai, Bangalore (IN); Jose Enrique Montero Casimiro, Havana (CU)

(73) Assignee: BIOCON LIMITED (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/819,351

(22) Filed: Nov. 21, 2017

(65) Prior Publication Data

US 2018/0087080 A1   Mar. 29, 2018

Related U.S. Application Data

(63) Continuation of application No. 14/905,350, filed as application No. PCT/IB2014/063348 on Jul. 23, 2014, now Pat. No. 9,856,502.

(30) Foreign Application Priority Data

Jul. 23, 2013  (IN) ............................ 3262/CHE/2013
Jul. 23, 2013  (IN) ............................ 3265/CHE/2013

(51) Int. Cl.
  *A61K 39/00*  (2006.01)
  *C07K 16/00*  (2006.01)
  *C07K 16/28*  (2006.01)
  *C12P 21/00*  (2006.01)

(52) U.S. Cl.
  CPC ............ *C12P 21/005* (2013.01); *C07K 16/00* (2013.01); *C07K 16/2896* (2013.01); *A61K 2039/505* (2013.01); *C07K 2317/24* (2013.01); *C07K 2317/41* (2013.01); *C07K 2317/54* (2013.01); *C07K 2317/72* (2013.01); *C07K 2317/73* (2013.01); *C07K 2317/732* (2013.01); *C07K 2317/92* (2013.01); *C07K 2319/30* (2013.01); *Y02A 50/407* (2018.01)

(58) Field of Classification Search
  None
  See application file for complete search history.

(56) References Cited

U.S. PATENT DOCUMENTS

| | | |
|---|---|---|
| 5,223,409 A | 6/1993 | Ladner et al. |
| 5,859,205 A | 1/1999 | Adair et al. |
| 6,248,516 B1 | 6/2001 | Winter et al. |
| 6,300,064 B1 | 10/2001 | Knappik et al. |
| 6,331,415 B1 | 12/2001 | Cabilly et al. |
| 6,372,215 B1 | 4/2002 | Starling et al. |
| 6,548,640 B1 | 4/2003 | Winter |
| 7,972,810 B2 | 7/2011 | Crowell et al. |
| 2003/0204862 A1 | 10/2003 | Kuehn et al. |
| 2009/0208500 A1 | 8/2009 | Joly et al. |
| 2012/0277165 A1 | 11/2012 | Collins et al. |

FOREIGN PATENT DOCUMENTS

| | | |
|---|---|---|
| WO | WO2010141855 | 12/2010 |
| WO | WO 2011127322 | 10/2011 |

OTHER PUBLICATIONS

Biocon Press Release, Biocon Receives Marketing Authorization for its Novel Biologic Itolizumab for Psoriasis, Jan. 8, 2013.
Shitara, K. Potelligent Antibodies as Next Generation Therapeutics Antibodies, *The Pharmaceutical Society of Japan*, 2009, vol. 129, pp. 3-9.
Anumula, K.A. New high-performance liquid chromatography assay for glycosyltransferases based on derivatization with anthranilic acid and fluorescence detection, *Glycobiology*, 2012, vol. 22, No. 7, pp. 912-917.
Aruffo, A. et al. The Lymphocyte Glycoprotein CD6 Contains a Repeated Domain Structure Characteristics of a New Family of Cell Surface and Secreted Proteins, *J. Exp. Med.*, Oct. 1991, vol. 174, pp. 949-952.
Costa, Ana Rita, et al. The impact of microcarrier culture optimization on the glycosylation profile of a monoclonal antibody, *Springerplus*, (2013) vol. 2, No. 1, 1-10.
Friedman, J. et al. Cloning and characterization of cyclophilin C-associated protein: A candidate natural cellular ligand for cyclophilin C, *Proc. Natl. Acad. Sci.*, 1993, vol. 90. pp. 6815-6819.
Goldberger, G. et al. Human Complement Factor I: Analysis of cDNA-derived Primary Structure and Assignment of Its Gene to Chromosome4*, *The Journal of Biological Chemistry*, 1987, vol. 262, No. 21, pp. 10065-10071.
Jayaraman, K. Biocon's first-in-class anti-CD6 mAv reaches the market, *Nature Biotechnology*, Dec. 2013, vol. 31, No. 12, pp. 1062-1063.
Jones, N. H. et a. Isolation of complementary DNA clones encoding the human lymphocyte glycoprotein T1/Leu-1, *Nature*, 1986, vol. 323, No. 25, pp. 346-349.
Kamoun, M. et al. A Novel human T cell antigen preferentially expressed on mature T cells and shared by both well and poorly differentiated B cell leukemias and lymphomas, *The Journal of Immunology*, 1981, vol. 127, No. 3, pp. 987-991.

(Continued)

Primary Examiner — Addison D Ault
(74) Attorney, Agent, or Firm — Marianne Fuierer; Olive Law Group, PLLC

(57) ABSTRACT

The present invention relates to a method or process for controlling, inhibiting or reducing protein fucosylation in a eukaryote and/or eukaryotic protein expression system. Said method comprises carrying out the protein expression and/or post-translational modification in the presence of an elevated total concentration of manganese or manganese ions.

5 Claims, 16 Drawing Sheets

(56) References Cited

OTHER PUBLICATIONS

Konno, Y. et al. Fucose content of monoclonal antibodies can be controlled by culture medium osmolality for high antibody-dependent cellular cytotoxicity, *Cytotechnology*, 2012, vol. 64, pp. 249-265.

Law. S.K. et al. A new macrophage differentiation antigen which is a member of the scavenger receptor superfamily, *Eur. J. Immunol.* 1993, vol. 23, pp. 2320-2325.

Matsumoto, A.K. et al. Intersection of the Complement and Immune Systems: A Signal Transduction Complex of the B Lymphocyte-containing Complement Receptor Type 2 and CD19, *J. Exp. Med.* 1991. vol. 173, pp. 55-64.

Mayer, B. et al. Expression of the CD6 T lymphocyte differentiation antigen in normal human brain, *Journal of Neuroimmunology*, 1990, vol. 29, pp. 193-202.

Moloney, D. et al. The O-linked fucose glycosylation pathway: identification and characterization of a uridine diphosphoglucose: fucose-beta1,3-glucosyltransferase activity from Chinese hamster ovary cells, *Glycobiology*, (1999) vol. 9, No. 7, 679-687.

Nahrgang, Sefan. Influence of cell-line and process conditions on the glycosylation of Recombinant Proteins, http://infoscience.epfl.ch/record/33084/files/EPEL_TH2608.pdf (2002).

Nair, P. et al. The inhibition of T cell proliferation in a mixed lymphocyte reaction by Itolizumab (T1h) is associated with reduction in pro inflammatory cytokines and CD6 internalization, *The Journal of Immunology*, 2011, vol. 186, No. 1, pp. 1-2.

Niwa, R. et al. Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma, Cancer Research, 2004, vol. 64, pp. 2127-2133.

Resnick, D. et al. The SRCR superfamily: a family reminiscent of the Ig superfamily, *TIBS* 19, 1994, pp. 5-8.

Rodriguez, Pedro C. et al. A clinical exploratory study with itolizumab, an anti-CD6 monoclonal antibody, in patients with rheumatoid arthritis, *Results in Immunology* 2 (2012) 204-211.

Shields, R.L. et al. Lack of Fucose on Human IgG1 N-Linked Oligosaccharide Improves Binding to Human $Fc_\gamma RIII$ and Antibody Dependent Cellular Toxicity, *The Journal of Biological Chemistry*, 2002, vol. 277, No. 30, pp. 26733-26740.

Wijngaard, P.L. et al. Molecular characterization of the WC1 antigen expresses specifically on bovine CD4-CD8-gamma delta T lymphocytes, *J Immunol* 1992, vol. 149, pp. 3273-3277.

Xing, Z. et al. Optimizing amino acid composition of CHO cell culture media for a fusion protein production, *Proc Biochem*, (2011), vol. 46, No. 7, pp. 1423-1429.

METHODS FOR CONTROLLING FUCOSYLATION LEVELS IN PROTEINS

CROSS-REFERENCE TO RELATED APPLICATIONS

This is a continuation application of U.S. patent application Ser. No. 14/905,350, filed on Jan. 15, 2016, now U.S. Pat. No. 9,856,502, which was filed under the provisions of 35 U.S.C. § 371 and claims the priority of International Patent Application No. PCT/IB2014/063348 filed on Jul. 23, 2014 which in turn claims the benefit of and the priority to provisional Indian Patent applications 3262/CHE/2013 filed on 23 Jul. 2013 and 3265/CHE/2013 filed on 23 Jul. 2013 with the Indian Patent Office. The content of the said applications filed on 23 Jul. 2013 is incorporated herein by reference for all purposes in its entirety, including an incorporation of any element or part of the decision, claims or drawings not contained herein and referred to in Rule 20.5(a) of PCT, pursuant to Rule 4.18 of the PCT.

TECHNICAL FIELD

The present invention relates to methods for controlling fucosylation levels in proteins.

BACKGROUND OF THE DISCLOSURE

Proteins expressed in eukaryotic expression systems undergo a process of post-translational modification, which involves glycosylation. Eukaryotic expression systems which have been established today for the production of glycoproteins, like IgG and other monoclonal antibodies comprising an Fc region add N-glycans to the polypeptide chains.

In IgG, the most important N-glycan is bound at Asn 297 of both $CH_2$ chains (see FIG. 14), which comprises, among others, N-acetyl-neuraminic acid (sialic acid), N-acetyl-glucosamine, galactose, mannose, and fucose residues.

This applies, basically, for transgenic plant expression systems as well as for mammalian cell lines, insect cell lines etc. In all these cases, the N-glycan comprises at least one fucose residue which is bound either α-3-glycosidically or α-6-glycosidically to the N-acetyl-glucosamine residue bound to the Asn residue of the polypeptide chain.

Yeast expression systems tend to produce hyperglycoproteins rich in mannose, which often lead to unwanted immune reactions when the therapeutic antibody is administered to a patient. Baculovirus transfected insect cell systems cause problems due to hypoglycosylation, which negatively affects the effector function of therapeutic antibodies. Furthermore, the major disadvantage are the catalytic properties of infectious baculovirus that narrows the window for full IgG production.

ADCC is a mechanism of cell-mediated immunity whereby an effector cell of the immune system actively lyses a target cell that has been bound by specific antibodies. It is one of the mechanisms through which antibodies, as part of the humoral immune response, can act to limit and contain infection. Classical ADCC-mediating effector cells are natural killer (NK) cells; but monocytes and eosinophils can also mediate ADCC. ADCC is part of the adaptive immune response due to its dependence on a prior antibody response.

Therapeutic antibodies which are used to elicit an ADCC in target cells need an Fc region in order to be recognized by Fc gamma receptors of the said effector cells.

Recent studies have shown that monoclonal antibodies having a reduced amount of fucose in its glycosylation pattern exhibit much higher Antibody-Dependent Cellular Cytotoxicity (ADCC) activity as compared to fucosylated antibodies. Again, it is basically position Asn 297 where a lack of fucose residues leads to the increased ADCC. The mechanism behind the increased ADCC of a low/no-fucose Antibody seems to be mediated by an increased affinity of a so modified Fc region to FcγR, for example FcγIIIa (CD 16), the major Fc receptor for ADCC in human immune effector cells (Shields et al, 2002).

Fucosylation is one of the most common modifications involving oligosaccharides on glycoproteins or glycolipids. Fucosylation comprises the attachment of a fucose residue to N-glycans, O-glycans, and glycolipids. O-Fucosylation, a special type of fucosylation, is very important for Notch signaling. The regulatory mechanisms for fucosylation are complicated. Many kinds of fucosyltransferases, the GDP-fucose synthesis pathway, and GDP-fucose transporter are involved in the regulation of fucosylation.

Glycosylation is known to impact the effector functions of therapeutic monoclonal antibodies. Among the various sugar residues in the oligosaccharide chain of an antibody, fucose is one of the key sugars that affects the antibody dependent cellular cytotoxicity (ADCC) induced by the product.

Manipulation of cell culture parameters is often employed to control galactosylation and sialylation of an antibody. Control of fucosylation is majorly done by using FUT8 knock out cells and other gene silencing models through cell line engineering.

US20090208500 discloses the production of antibodies with reduced fucose and improved Fc function by manipulation of FUT8 Knock out cells.

U.S. Pat. No. 7,972,810 discloses cell culturing methods and media containing manganese that improve glycosylation or sialylation of glycoproteins, including erythropoietin and analogs or derivatives thereof. According to the disclosure, manganese increases sialylation and site occupancy in case of O-linked and N-linked glycosylation (i.e. lower aglycosylated product) and also increases terminal galactosylation.

Further, fucose content of monoclonal antibodies can be controlled by culture medium osmolality for high antibody-dependent cellular cytotoxicity. (Konno et al. 2012)

Yet, there is a need for an efficient method of producing glycoproteins in a desired cell line while controlling the fucose content of the recombinantly engineered antibodies without undergoing the laborious process of creating a FUT8 gene knockout in a selected cell line each time.

EMBODIMENTS OF THE INVENTION

These objects are met with methods and means according to the independent claims of the present invention. The dependent claims are related to preferred embodiments. It is yet to be understood that value ranges delimited by numerical values are to be understood to include the said delimiting values.

SUMMARY OF THE DISCLOSURE

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

According to one embodiment of the invention, a method or process for modifying fucosylation in a eukaryote and/or a eukaryotic protein expression system is provided, in which method or process the total concentration of manganese or manganese ions in the medium is controlled.

Fucosylation of glycoproteins is accomplished by fucosyltransferases (FUT). These are enzymes that transfer an L-fucose sugar from a GDP-fucose (guanosine diphosphate-fucose) donor substrate to an acceptor substrate. The acceptor substrate can be another sugar such as the transfer of a fucose to a core GlcNAc (N-acetylglucosamine) sugar as in the case of N-linked glycosylation, or to a protein, as in the case of O-linked glycosylation produced by O-fucosyltransferase. There are various fucosyltransferases in mammals, the vast majority of which, are located in the Golgi apparatus. The O-fucosyltransferases have recently been shown to localize to the endoplasmic reticulum (ER). Examples of mammalian fucosyltransferases are FUT1; FUT2; FUT3; FUT4; FUT5; FUT6; FUT7; FUT8; FUT9; FUT10 and FUT11.

Manganese is an essential trace element which participates in many enzyme systems, although its role is not yet fully understood. It acts as a cofactor in enzymes that are essential for energy production and is involved in the metabolism of glucose, glycogen storage in the liver, protein digestion and synthesis of cholesterol and fatty acids. It is also essential for the synthesis of DNA and RNA molecules.

Manganese is essential for the growth and maintenance of the nervous system, the development and maintenance of bones and joints, the function of female sex hormones and thyroid hormones. Superoxide dismutase (SOD, MnSOD) is an antioxidant enzyme that in its structure contains manganese.

In extracellular liquids or Eukaryotes, manganese is practically absent, while in mammals, the intracellular concentration of Manganese is in the range of 0.010 picogram/cell-0.10 picogram/cell.

However, the inventors surprisingly found that that the concentration of manganese has a direct effect on the fucosylation level of glycoproteins.

Thus, the present invention provides for modification of the fucose content of glycosylated proteins by varying the total concentration of manganese or manganese ions in media and feeds in the process.

Preferably, the method or process is a method or process to decrease fucosylation. In such method or process the protein expression and/or post-translational modification is carried out in the presence of an elevated total concentration of manganese or manganese ions.

Surprisingly, the inventors found that under such conditions, the glycoproteins expressed have a decreased fucosylation level. Further, they found that the cell growth, viability and the titre of the proteins produced is not effected by the elevation of manganese or manganese ion concentration.

Further, they found that other properties of the glycosylation pattern, namely G0 and Man5, are increased in the presence of an elevated total concentration of manganese or manganese ions.

BRIEF DESCRIPTION OF THE FIGURES

FIG. 5b shows the analysis of the experiments shown in FIG. 5a.

DETAILED DESCRIPTION OF THE INVENTION

Figure 1:
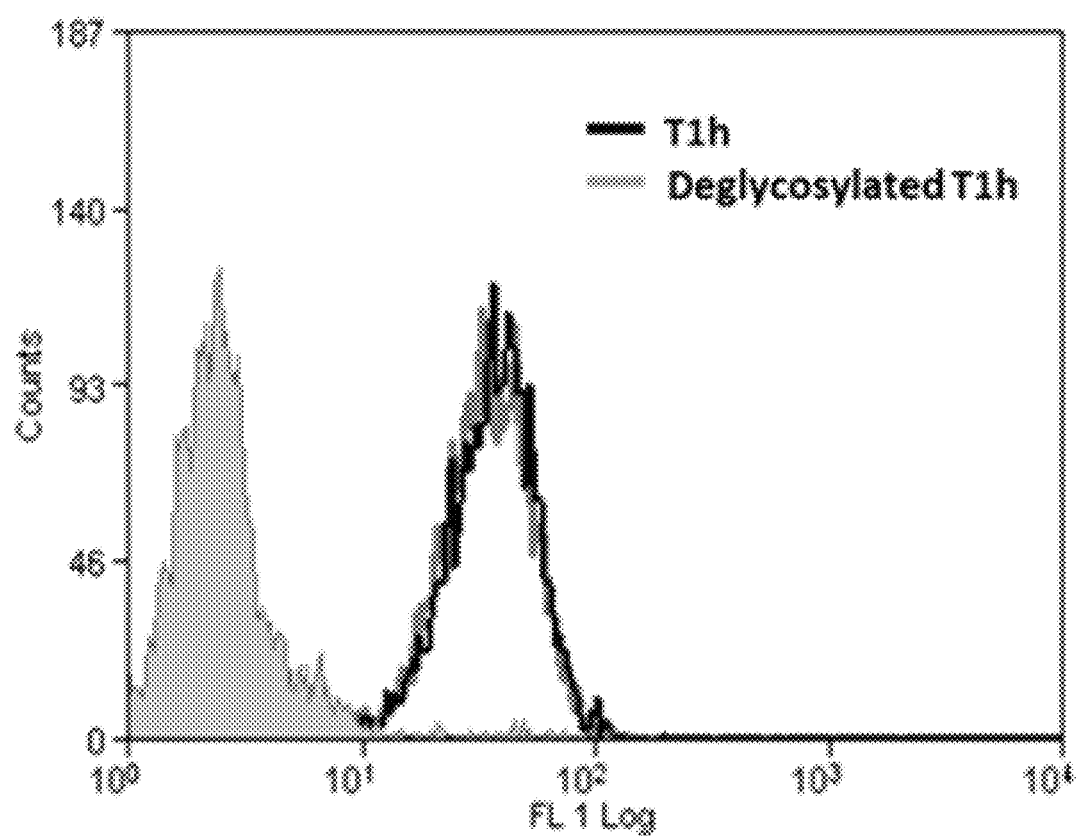
FIG. 1 shows the results of a deglycosylation experiment carried out with an antibody having an Fc region.

As used herein, the term "fucosylation level" refers to the total amount of glycoproteins in which the glycans carry a fucose. Likewise, the terms "afucosylation level" and "% afucosylation" refers to the percentage of glycoprotein which have no fucose in their glycans.

In a preferred embodiment of the method or process according to the invention, it is provided that the elevated concentration of manganese or manganese ions is in the range of >0.05 mM-<10 mM.

Preferably, the elevated concentration of manganese or manganese ions is 0.05; 0.1; 0.15; 0.2; 0.25; 0.3; 0.35; 0.4; 0.45; 0.5; 0.55; 0.6; 0.65; 0.7; 0.75; 0.8; 0.85; 0.9; 0.95; 1; 1.05; 1.1; 1.15; 1.2; 1.25; 1.3; 1.35; 1.4; 1.45; 1.5; 1.55; 1.6; 1.65; 1.7; 1.75; 1.8; 1.85; 1.9; 1.95; 2; 2.05; 2.1; 2.15; 2.2; 2.25; 2.3; 2.35; 2.4; 2.45; 2.5; 2.55; 2.6; 2.65; 2.7; 2.75; 2.8; 2.85; 2.9; 2.95; 3; 3.05; 3.1; 3.15; 3.2; 3.25; 3.3; 3.35; 3.4; 3.45; 3.5; 3.55; 3.6; 3.65; 3.7; 3.75; 3.8; 3.85; 3.9; 3.95; 4; 4.05; 4.1; 4.15; 4.2; 4.25; 4.3; 4.35; 4.4; 4.45; 4.5; 4.55; 4.6; 4.65; 4.7; 4.75; 4.8; 4.85; 4.9; 4.95; 5; 5.05; 5.1; 5.15; 5.2; 5.25; 5.3; 5.35; 5.4; 5.45; 5.5; 5.55; 5.6; 5.65; 5.7; 5.75; 5.8; 5.85; 5.9; 5.95; 6; 6.05; 6.1; 6.15; 6.2; 6.25; 6.3; 6.35; 6.4; 6.45; 6.5; 6.55; 6.6; 6.65; 6.7; 6.75; 6.8; 6.85; 6.9; 6.95; 7; 7.05; 7.1; 7.15; 7.2; 7.25; 7.3; 7.35; 7.4; 7.45; 7.5; 7.55; 7.6; 7.65; 7.7; 7.75; 7.8; 7.85; 7.9; 7.95; 8; 8.05; 8.1; 8.15; 8.2; 8.25; 8.3; 8.35; 8.4; 8.45; 8.5; 8.55; 8.6; 8.65; 8.7; 8.75; 8.8; 8.85; 8.9; 8.95; 9; 9.05; 9.1; 9.15; 9.2; 9.25; 9.3; 9.35; 9.4; 9.45; 9.5; 9.55; 9.6; 9.65; 9.7; 9.75; 9.8; 9.85; 9.9; 9.95; or 10 mM.

These concentrations refer to the total concentration in the medium where the protein expression and/or post-translational modification takes place. This means that, e.g., feed solutions can have significantly higher concentration of manganese or manganese ions.

Preferably, the concentration of manganese is accomplished by adding manganese to the culture medium, and/or to the feed medium.

Likewise preferably, the manganese concentration is increased or decreased during protein expression and/or post-translational modification.

In a preferred embodiment of the method or process according to the invention, it is provided that the protein expression and/or post-translational modification is carried out in a protein expression system selected from the group consisting of Insect cells
Fungal cells
Yeast cells
Protozoan cells, and/or
Mammalian cells.

Preferably, the mammalian cells are selected from the group consisting of murine cells (e.g., NSO), hamster cells (e.g., CHO or BHK) and/or human cells (e.g., PER.C6).

Preferably, the protein is a glycoprotein. More preferably, the protein is a recombinant protein.

In a preferred embodiment of the method or process according to the invention, it is provided that the protein is an immunoligand.

The term "immunoligand" is used herein to mean an entity that has the capability to bind to another biological entity with a sufficient degree of sensitivity and/or specificity.

In another preferred embodiment of the method or process according to the invention, it is provided that immunologand is at least one selected from the group consisting of a monoclonal antibody (murine, chimeric, humanized, human), or derivative thereof a
a new antibody format
a fusion peptide consisting of an immunoglobulin Fc region fused to a target binding moiety, e.g., a receptor fragment The above listed immunoligands comprise, preferably, an Fc region or another domain that is capable of being glycosylated and/or binding to an Fc receptor, e.g., FcγRI (CD64), FcγRIIA (CD32), FcγRIIB (CD32), FcγRIIIA (CD 16a), FcγRIIIB (CD 16b).

As used herein, the term "monoclonal antibody (mAb)", shall refer to an antibody composition having a homogenous antibody population, i.e., a homogeneous population consisting of a whole immunoglobulin, or a fragment or derivative thereof. Particularly preferred, such antibody is selected from the group consisting of IgG, IgD, IgE, IgA and/or IgM, or a fragment or derivative thereof.

As used herein, the term "derivative" shall refer to protein constructs being structurally different from, but still having some structural relationship to, the common antibody concept.

Methods for the production and/or selection of chimeric, humanised and/or human mAbs are known in the art. For example, U.S. Pat. No. 6,331,415 by Genentech describes the production of chimeric antibodies, while U.S. Pat. No. 6,548,640 by Medical Research Council describes CDR grafting techniques and U.S. Pat. No. 5,859,205 by Celltech describes the production of humanised antibodies. In vitro antibody libraries are, among others, disclosed in U.S. Pat. No. 6,300,064 by MorphoSys and U.S. Pat. No. 6,248,516 by MRC/Scripps/Stratagene. Phage Display techniques are for example disclosed in U.S. Pat. No. 5,223,409 by Dyax.

Transgenic mammal platforms are for example described in US200302048621 by TaconicArtemis.

The term "new antibody format" encompasses, for example bi- or trispecific antibody constructs, Diabodies, Camelid Antibodies, Domain Antibodies, bivalent homodimers with two chains consisting of scFvs, IgAs (two IgG structures joined by a J chain and a secretory component), shark antibodies, antibodies consisting of new world primate framework plus non-new world primate CDR, dimerised constructs comprising CH3+VL+VH, and antibody conjugates (e.g., antibody or fragments or derivatives linked to a toxin, a cytokine, a radioisotope or a label). This list is however not restrictive.

Further, the term also encompasses immunotoxins, i.e., heterodimeric molecules consisting of an antibody, or a fragment thereof, and a cytotoxic, radioactive or apoptotic factor. Such type of format has for example been developed by Philogen (e.g., anti-EDB human antibody LI 9, fused to human TNF), or Trastuzumab emtansine (T-DM1), which consists of trastuzumab linked to the cytotoxoic Mertansine (DM1).

The term "fusion peptide" or "fusion protein" proteins relates, for example, to proteins consisting of an immunoglobulin Fc portion plus a target binding moiety (so-called-cept molecules).

In another preferred embodiment of the method or process according to the invention, it is provided that the immunoligand has a reduced degree of fucosylation compared to an immunoligand expressed in the absence of an elevated concentration of manganese or manganese ions.

Preferably, the degree of fucosylation is determined by methods according to the art. Such methods comprise, among others, digestion with Peptide-N-Glycosidase F (PN-Gase F), to deglycosylate the antibodies (see description at FIG. 1 for more details), and subsequent collection of the isolated glycanes. The collected glycanes are labeled with anthranicilic acid and then analyzed by means of NP HPLC. Full details of the method are disclosed in Anumula (2012), content of which is incorporated herein by reference.

The term "absence of an elevated concentration of manganese or manganese ions." means that during the process or in the preparation of the process, no manganese or manganese ions have willingly been introduced. This does not exclude that traces of manganese naturally occurring in media like water can still be present.

In a preferred embodiment of the method or process according to the invention, it is provided that the immunoligand demonstrates an increased ADCC activity compared to an immunoligand (i) expressed in the absence of an elevated concentration of manganese or manganese ions or (ii) having a higher degree of fucosylation.

The term "ADCC" relates to a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is part of the adaptive immune response due to its dependence on a prior antibody response.

Figure 3:
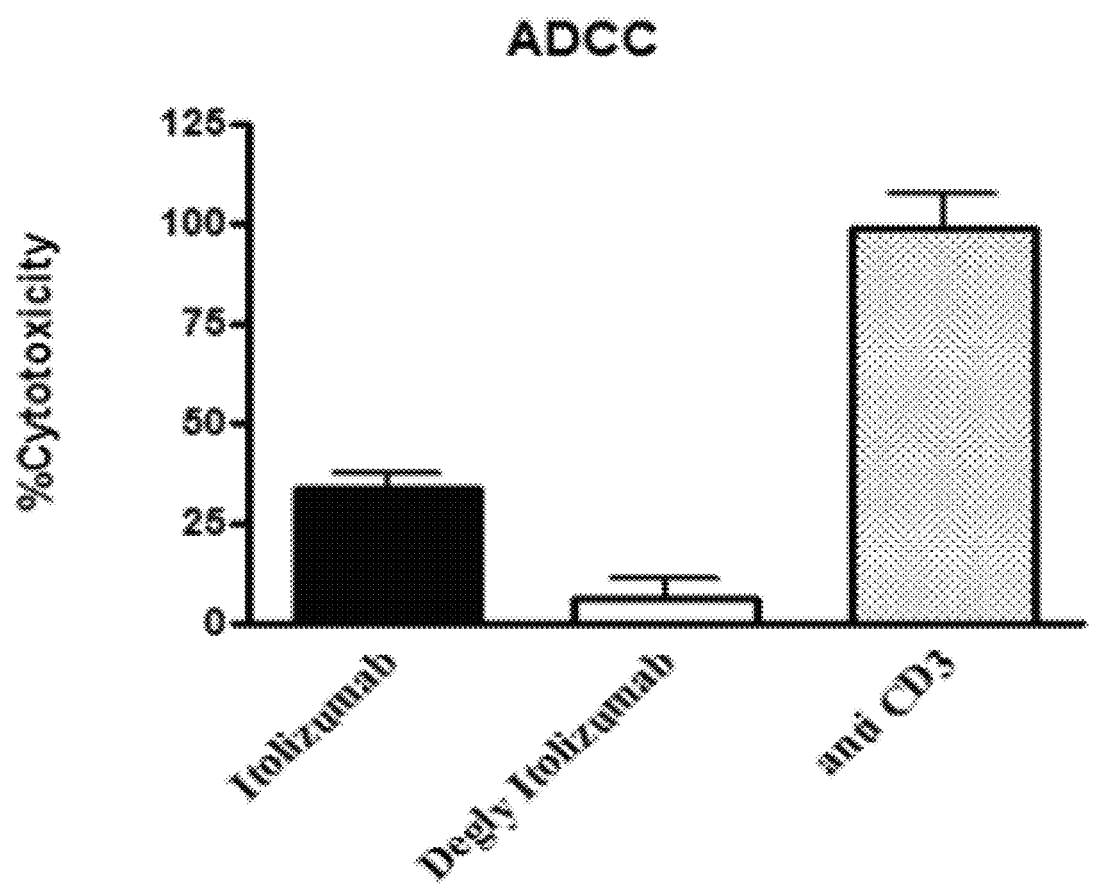
FIG. 3 shows the results of a cytotoxicity assay comparing native antibody and deglycosylated antibody.

Preferably, the ADCC activity is determined by methods according to the art. Such methods comprise, among others, the cytotoxicity assay as shown in FIG. 3.

Other suitable assays include include chromium-51 [Cr51] release assay, europium [Eu] release assay, and sulfur-35 [S35] release assay. Usually, a labelled target cell line expressing a certain surface-exposed antigen is incubated with antibody specific for that antigen. After washing, effector cells expressing Fc receptor CD 16 are co-incubated with the antibody-labelled target cells. Target cell lysis is subsequently measured by release of intracellular label by a scintillation counter or spectrophotometry. The coupled bioluminescent method aCella TOX is now in widespread use for ADCC and other cytotoxicity assessments. Since this technique measures the release of enzymes naturally present in the target cells, no labeling step is required and no radioactive agents are used.

Preferably, the immunoligand targets one or more cellular surface antigens involved in cell-mediated immune defense.

Preferably, said cellular surface antigens are selected from the group consisting of cyclophilin C, complement factor I, CD6, CD5, bovine WC-1 and M130.

CD6 is an important cell surface protein predominantly expressed by human T cells and a subset of B cells, as well as by some B cell chronic lymphocytic leukemias and neurons (Aruffo et al. 1991, Kantoun et al. 1981, Mayer et al. 1990). CD6 is a member of a large family of proteins characterized by having at least one domain homologous to the scavenger receptor cysteine-rich domain (SRCR) of type I macrophages (Matsumoto et al. 1991 and Resnick et al. 1994). Other members of this family include CD5 (Jones et al., 1986) cyclophilin C (Friedman et al. 1993), complement factor I, which binds activated complement proteins C3b and C4b (Goldberger, et al., J. Biol. Chem. 1987, 262: 10065), bovine WC-1 expressed by .tau./.delta. T cells (Wijingaard et al. 1992) and Ml 30 (Law et al. 1993), a macrophage activation marker.

Other preferred surface antigens encompass CD20, EGFR, HER2/neu, and membrane-bound TNF.

In a preferred embodiment of the method or process according to the invention, it is provided that the immunoligand is Itolizumab.

Itolizumab (INN, trade name Alzumab®) is a 'first in class' humanized IgG1 monoclonal antibody developed by Biocon. It selectively targets CD6, a pan T cell marker involved in co-stimulation, adhesion and maturation of T cells. Itolizumab, by binding to CD6, down regulates T cell activation, causes reduction in synthesis of pro-inflammatory cytokines and possibly plays an important role by reducing T cell infiltration at sites of inflammation. A double blind, placebo controlled, phase III treat-Plaq study of itolizumab successfully met the pre-specified primary endpoint of significant improvement in PASI-75 (Psoriasis Area and Severity Index) score after 12 weeks of treatment in patients with moderate to severe psoriasis compared to placebo. Biocon received marketing authorization for the drug from the Drugs Controller General of India (DCGI) in January 2013 and marketing within India commenced in August 2013 (Jayaraman, 2013).

Itolizumab is produced from mouse derived NSO cell line (called herein "Tlh") and also from Chinese Hamster Ovary (CHO) cell line (called herein "Bmab-600"). The Fc portions of Bmab-600 and Tlh bind to FcγRIIIa with different affinities as the post translational modifications, especially the afucosylation pattern varies with cell line and culture conditions.

Itolizumab can for example be produced from mouse derived NSO cell line (called herein "Tlh") and also from Chinese Hamster Ovary (CHO) cell line (called herein "Bmab-600"). The Fc portions of Bmab-600 and Tlh bind to FcγRIIIa with different affinities as the post translational modifications, especially the afucosylation pattern varies with cell line and culture conditions.

According to another aspect of the invention, a glycoprotein is provided, which glycoprotein is produced with a method or process according to any of the method or process of the invention.

Preferably, said glycoprotein is a recombinant protein. More preferably, said glycoprotein is an immunoligand, preferably an antibody. It is particularly preferred that said glycoprotein has a decreased fucose content in its glycosylation pattern.

Preferably, the glycoprotein, or a subdomain thereof, like an Fc region, has an afucosylation level of around 35%.

In a preferred embodiment, it is provided that the glycoprotein has an increased ADCC. Preferably, said glycoprotein is Itolizumab.

In another preferred embodiment, it is provided that the glycoprotein effects in vitro- or in vivo reduction of cells being positive for CD25 and CD4, in particular of CD4+ T cells.

The inventors have surprisingly shown that the use of anti-CD6 antibody according to the invention leads to reduced proliferation of cells which are positive for the surface antigens CD25 and CD4 (see FIG. 5B and description), in particular CD4+ T-Cells.

The term "reduction of cells", as used herein, refers to (i) the inhibition of proliferation, (ii) the depletion, (iii) induction of apoptosis or (iv) other mechanisms which lead to a reduction of such cells.

According to another aspect of the invention, the use of a glycoprotein as set forth above for the manufacture of a medicament for the treatment of a human or animal patient is provided. Likewise, the use of a glycoprotein as set forth above for the treatment of a human or animal patient is provided.

In a preferred embodiment of such use, the human or animal patient suffers from or has been diagnosed to be at risk to develop a disease selected from the group consisting of Neoplastic diseases, including tumors, lymphomas and leukemias, in particular B-cell chronic Lymphocytic leukemia (B-CLL), particularly T-cell leukemias Autoimmune disease, including Rheumatoid arthritis, Psoriasis, Crohn's disease, Lupus erythematosus, and/or Sjogren's disease Neurodegenerative diseases, including Multiple sclerosis, and/or Parkinson's disease, Alzheimer's disease, Huntington's disease and/or Amyotrophic lateral sclerosis, and/or Infectious diseases Preferably, such use relates to the treatment or prevention of averse adverse reactions like GVHD (Graft vs. Host disease) in a human or animal that has been transplanted. Such transplantation includes organ transplants as well as bone marrow transplants.

EXPERIMENTS AND FIGURES/EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

FIG. 1: Results of a deglycosylation experiment carried out with an antibody having an Fc region.

The anti CD antibody Itolizumab (also called Tlh), has been incubated with a deglycosylation buffer (50 mM Tris, ImM CaCl2, pH=8.1) in a 1:1 ratio to Itolizumab (5 mg/ml) followed by 24 hours incubation of Peptide-N-Glycosidase F (PNGase) enzyme (10 U for 1 mg antibodies).

After incubating for 24 hrs at 37° C., an equal volume of Tlh buffer (Histidine Trehalose buffer) in sample is added and centrifuged in centricon tubes (50 kD cut off filters) at 4° C., 4000 rpm for 15 minutes. The residual volume is re-suspended again in equal volume with Tlh buffer and centrifuged at 4° C., 4000 rpm for 15 minutes. The deglycosylated Ab is stored in final storage tube and concentration estimated by Nano drop. The deglycoslation is confirmed by CE-SDS (Capillary Electrophoresis). FACS (Fluorescence activated cell sorter) analysis has then been carried out. Briefly, HUT78 cells (T cells line) are labelled with the anti CD6 antibody Tlh, or the deglycosylated Tlh antibody produced as described above.

Subsequently coming with a secondary anti Fc antibody, labelled with FITC, a signal is observed. FIG. 1 shows that deglycosylation of the Fc region of Thl does not compromise its ability to bind to CD6 expressing cell lines. These results have further been confirmed by Plasmon resonance experiments.

Figure 2:
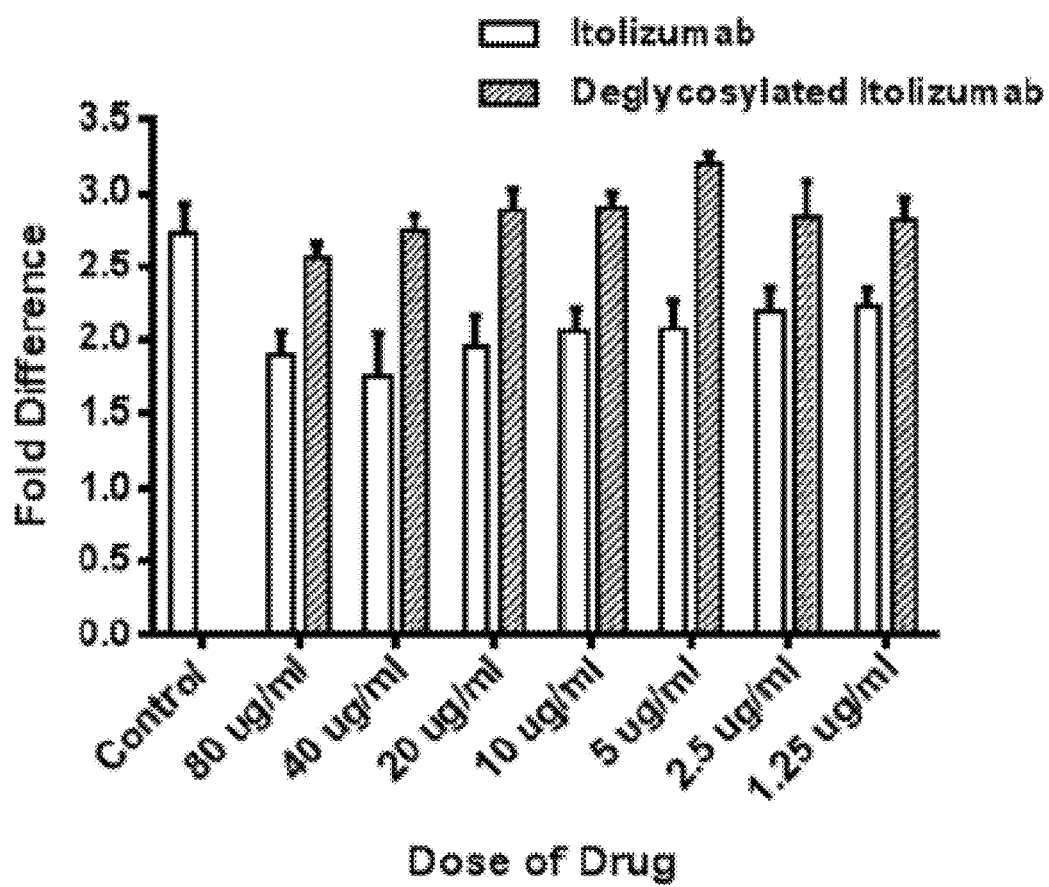
FIG. 2 shows the result of a deglycosylation experiment carried out with an antibody having an Fc region.

FIG. 2: Result of a deglycosylation experiment carried out with an antibody having an Fc region.

In particular, the anti CD antibody Itolizumab was deglycosylated as discussed supra. It's ability to inhibit of proliferation of activated T cells was then compared with that of unmodified Tlh in a suitable proliferation assay. Nimotuzumab, which is an antibody that has the same IgG backbone as that of Itolizumab but binds to EGFR, was used as negative control.

Briefly, the antibody was coated on sterile 96 well plates in a concentration range 0-^g/ml overnight with bicarbonate buffer at pH 9.5. After washes purified lymphocytes from normal healthy volunteers were added to the plates. Itolizumab from 80-1 μg/ml was added and the culture was incubated for 4 days. Alamar blue was added to measure proliferation. Fold difference is calculated relative to unstimulated cells control. Isotype Nimotuzumab antibody was used as control. Plate bound anti CD3 (the anti CD3 used is OKT3 clone manufactured at center for molecular immunology, Cuba) stimulates the proliferation of naive T cells (Peripheral Blood Mononuclear Cells (PBMC) from a human donor, purified over a density gradient of Ficoll) from normal healthy volunteers.

Nimotuzumab (8 ug/ml) does not show any inhibition of the T-Cell proliferation, resulting in about 2.75 fold increase in cells relative to unstimulated cells, while native Tlh shows inhibition of the T-Cell proliferation (35-20% inhibition in the 80 μg/ml-1.25 μg/ml range). In contrast thereto, the impact of deglycosylated Tlh is similar to that of Nimotuzumab. This means that upon deglycosylating, the antibody loses its ability to inhibit the proliferation of T cells.

FIG. 3: Results of a cytotoxicity assay comparing native antibody and deglycosylated antibody.

Frozen PBMCs were thawed in RPMI 1640 Media with 10% FBS in presence of IL-2 (Conc. 2.5 ng/mL) and incubated overnight in a 37° C., 5% $CO_2$ incubator. On the next day cells were resuspended in media without IL-2 and incubated for 4-5 hrs. In a 96 well plate 12,000 Hut-78 cells/50 μL were added to each well. 50 μL 3× concentrated drug (either native Tlh, deglycosylated Tlh or anti CD3 at 10 microgram/ml) as per template were added and incubated for 2 hours at 37° C., 5% $CO_2$ incubator. PBMCs were resuspended in assay media and 240,000 PBMCs/50 μL/well were added, to obtain a target to effector ratio of 1:20. The plates were incubated at 37° C., 5% $CO_2$ incubator for 22 hours. 50 μL of Cyto Tox-Glo was added to the plates and incubated for 30 minutes at room temperature. The plates were read using Spectramax for luminescence to determine the cytotoxicity.

While native Tlh shows mild but statistically consistent Antibody Dependent Cellular Cytotoxicity (ADCC) activity relative to anti CD3, which is a partially depleting antibody targeting T cells, this ADCC activity is significantly reduced on deglycosylation of the molecule, indicating the effector function of Tlh. Use of Fab2 fragment of Itolizumab can also reduce the ADCC activity comparable to the deglycosylated molecule.

Figure 4:
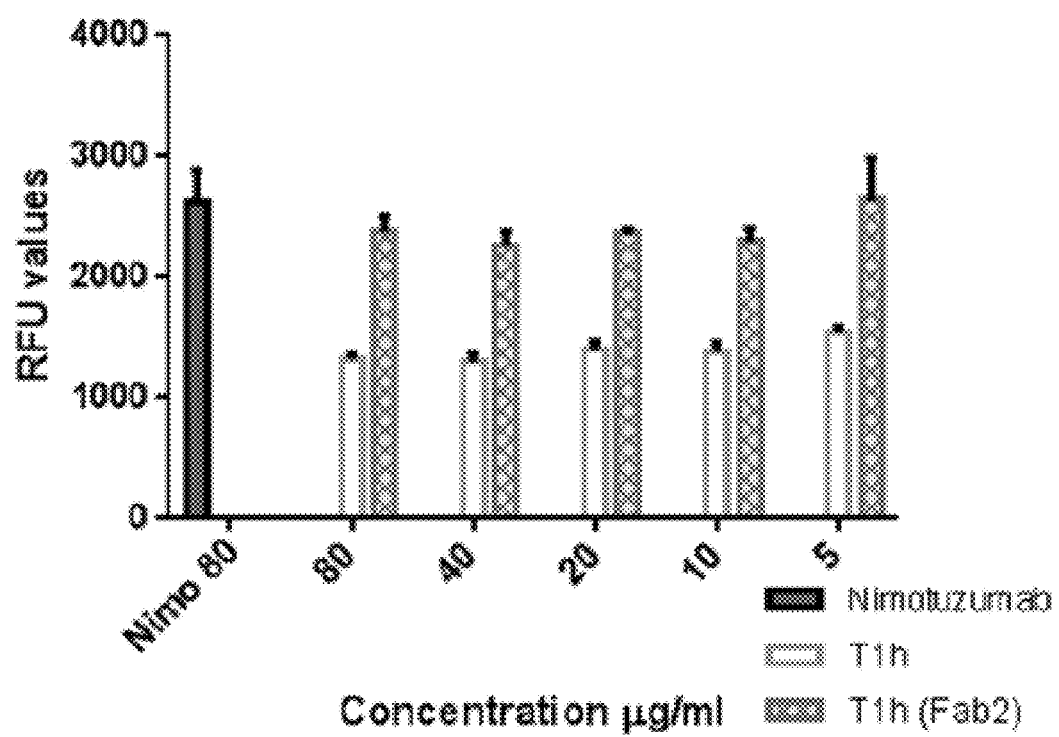
FIG. 4 shows the results of a Mixed Lymphocyte Reaction (MLR) experiment comparing native antibody and deglycosylated antibody.

FIG. 4: Results of a Mixed Lymphocyte Reaction (MLR) experiment comparing native antibody and deglycosylated antibody.

Preparation of PBMCs: 30 ml of blood was collected from a healthy donor. PBMCs were isolated by standard FICOLL density gradient centrifugation Monocyte Depletion & Setting up Dendritic Cell (DC) Derivation Assay: These cells were incubated in a $CO_2$ incubator for two hours. Monocytes were allowed to adhere onto the plastic surface. The non-adhered cells (PBLs) were subsequently removed from the flasks. All the flasks were washed with 1×PBS once. 20 ml of DC media (made 50 ml stock, 10 μL of Granulocyte macrophage colony-stimulating factor (GMCSF) and 5 μL of IL-4 in 50 ml of assay media) was added to each flask. The flasks were kept in $CO_2$ incubator for 6 days.

LPS Treatment to on-growing Dendritic Cells: At day 6, DC media with LPS (Lipopolysaccharides) was added to each flask (final concentration of LPS in the flask is 4 ug/ml) and kept back in $CO_2$ incubator for 40-48 hrs.

Preparation of DCs: After LPS treatment the cell suspension (DC) was collected from the two flasks. Each flask was washed with 1×PBS once. The cell suspension was spun down at 1500 rpm for 5 minutes and reconstituted in 3 ml media. LPS treated DCs were counted and reconstituted in media as per assay requirement.

Preparation of PBLs: Following the same protocol as mentioned before, Ficoll separation was performed after collecting blood from another healthy individual. After monocyte depletion the non adhered Peripheral blood lymphocytes (PBLs) were collected and spun down at 1500 rpm for 5 minutes and reconstituted in 5 ml media. PBLs were counted and reconstituted to $1.0 \times 10^6$ cells/ml.

SEB treatment to Dendritic Cells (DC): Staphylococcal enterotoxin B (SEB) stock concentration is 1 mg/ml. From the stock 3 μl of SEB is dissolved in 3 ml of media to get 1 mg/ml working solution of SEB. As per the standardized protocol $0.06 \times 10^6$ DCs are treated with 0.6 ug of SEB. A stock $0.1 \times 10^6$ cells/ml (LPS treated matured DCs) is made. From this, 600 μl of cell suspension is dissolved in 2.4 ml of assay media (total volume of cell suspension is 3 ml that contains $0.02 \times 10^6$ cells/ml). This is spun down at 1500 rpm for 5 min and 600 ml of SEB (1 ug/ml) is added to the pellet. This is incubated inside $CO_2$ incubator at 37° C. for 20 minutes. Excess media (2 ml) is added to the tube after incubation and washed at 1500 rpm for 5 min. Supernatant is discarded and the cells are washed again with 3 ml of media. Finally the pellet is dissolved in 3 ml of assay media.

Mytomycin C treatment to PBLs: 25 ug/ml Mytomycin solution is made from the Mytomycin stock of 1 mg/ml. $0.5 \times 10^6$ PBLs are treated with 500 μl of 25 μg/ml Mytomycin for 30 min inside $CO_2$ incubator at 37° C. Excess media (2 ml) is added to it after the incubation and the cells are washed at 1500 rpm for 5 media. Supernatant is discarded and the cells are washed again with 3 ml of media.

MLR Assay—Inhibition of Proliferation: MLR assay is performed at DC:PBL=1:50 ratio. Negative control used is Nimotuzumab. Native Tlh was tested against a Fab2 version thereof which lacks the fully functional Fc region. After 6 days the plate is read with alamar blue using Bio-Tek Synergy HT Gen5 plate reader.

While the intact antibody can inhibit the proliferation of T cells induced in this reaction, negative control Nimotuzumab with different specificity cannot. Tlh without the Fc region cannot inhibit the T cell proliferation either, suggesting that the glycosylated Fc region along with Fab is critical for the inhibitory capacity of Tlh in this assay. A similar effect has also been observed with the use of a deglycosylated Tlh thereby confirming the need of the glycosylation for the effector function of Tlh.

Figure 5A:
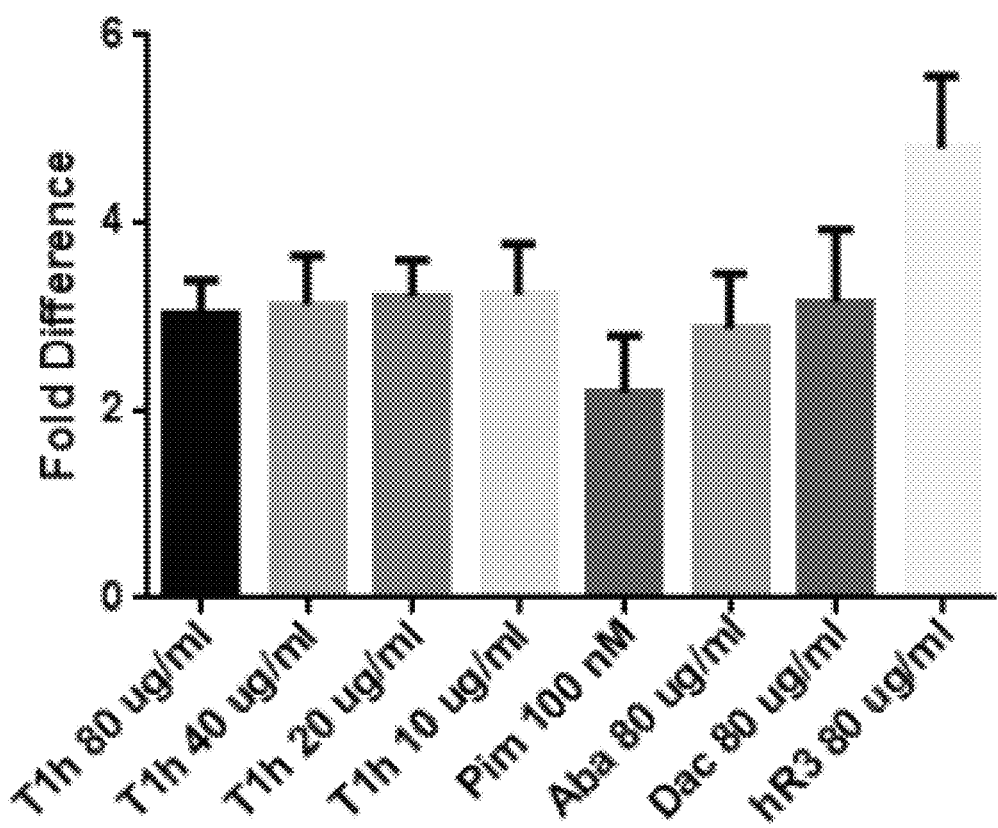
FIG. 5a shows the results of another Mixed Lymphocyte Reaction (MLR) experiment comparing different immunomodulators.

FIG. 5a: Results of another Mixed Lymphocyte Reaction (MLR) experiment comparing different immunomodulators.

The protocol is identical to FIG. 4. It is a mixed lymphocyte reaction. In addition to native Tlh at four concentrations other immunosuppressant and immunomodulators were used, namely pimecrolimus (Pim), Abatacept (Aba) and Daclizumab (Dac) are included as positive controls for the assay. Nimotuzumab (hR3) is used as a negative control. It turned out that Tl h is able to reduce the proliferation of T cells induced in a mixed lymphocyte reaction as compared to an isotype antibody, Nimotuzumab binding to Human EGFR. The fold reduction induced by Tlh is comparable to that induced by Abatacept (CTLA4-IgGlFc), Daclizumab (Anti CD25) and Pimecrolimus (small molecule, IL2 inhibitor).

Figure 5B:
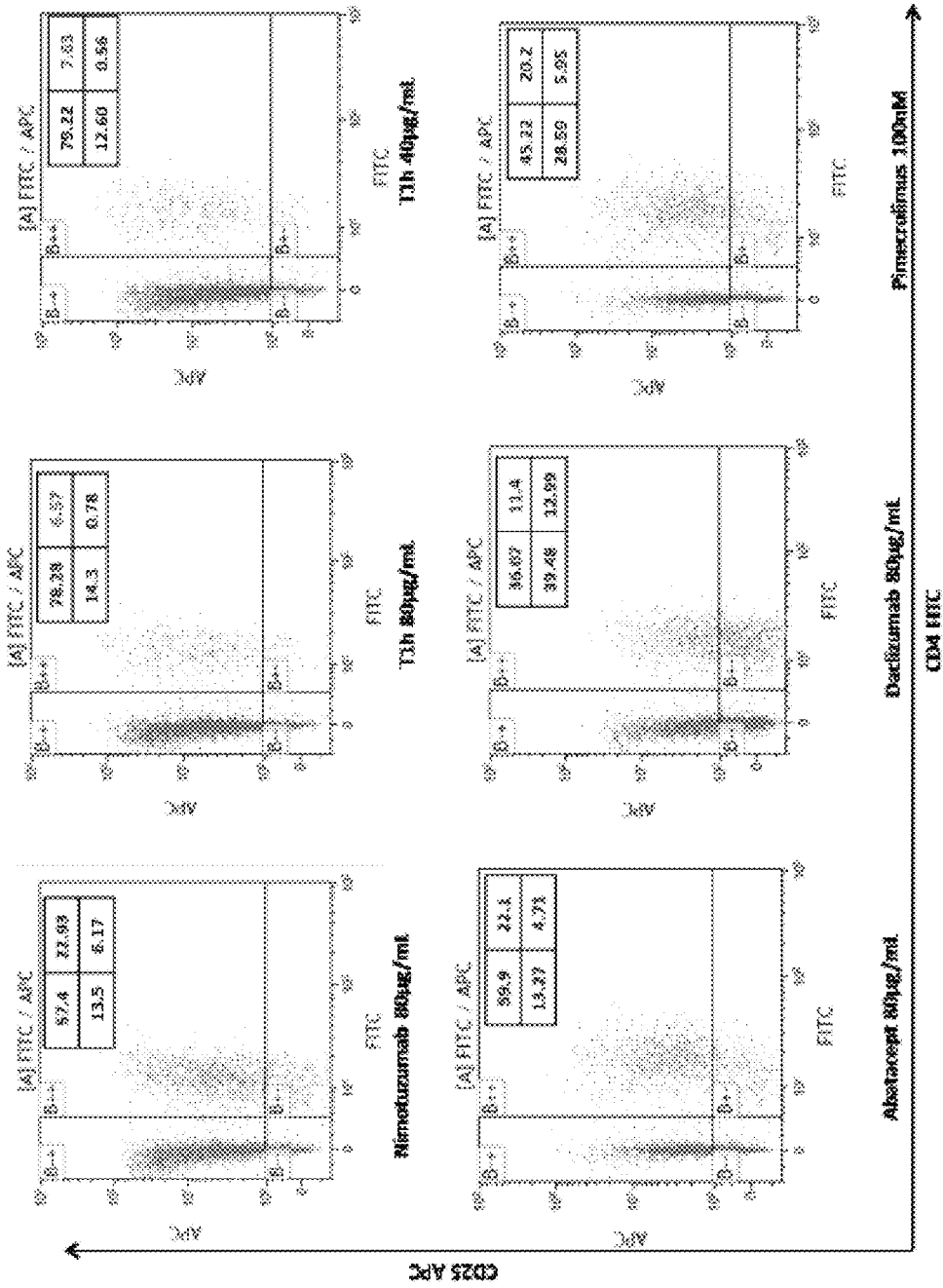

FIG. 5b: Analysis of the experiments shown in FIG. 5a.

The analysis relates to cells from the culture after 144 hours (6 days) in the mixed lymphocyte reaction. B--, B++, B+- and B-+ are are the quadrants. Here the cells in culture in an MLR are evaluated after 6 days. Although the inhibitory capacity of Tlh compares well with other antibodies, the path is different for Tlh as here unlike with the other molecules there is a significant decrease in CD4/CD25 activated T cell population. Tlh shows reduction in CD25+, CD4+ as well as CD4+ T cells. This indicates selective depletion of a subset of T cells. Hence, although as shown in FIG. 5 A, the inhibition in the MLR by Tlh is comparable to that of Daclizumab, Abatacept and Pimecrolimus, only Tlh shows a decrease in CD25+, CD4+ as well as CD4+ T cells.

Figure 6:
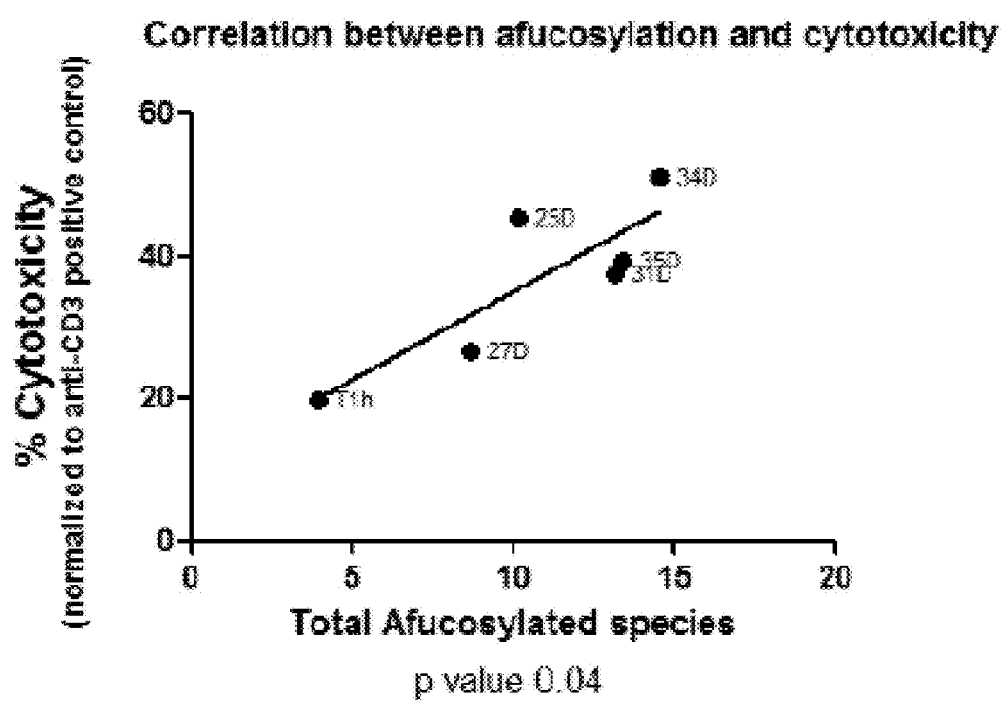
FIG. 6 shows the results of a cytotoxicity assay comparing native antibody and deglycosylated antibody.

FIG. 6: Results of a cytotoxicity assay comparing native antibody and deglycosylated antibody.

The same assay in FIG. 3 was used to evaluate the antibodies with different afucosylated content, compared to the positive control, anti-CD3. The data shown is a compilation from n=4 independent experiments.

Figure 11:
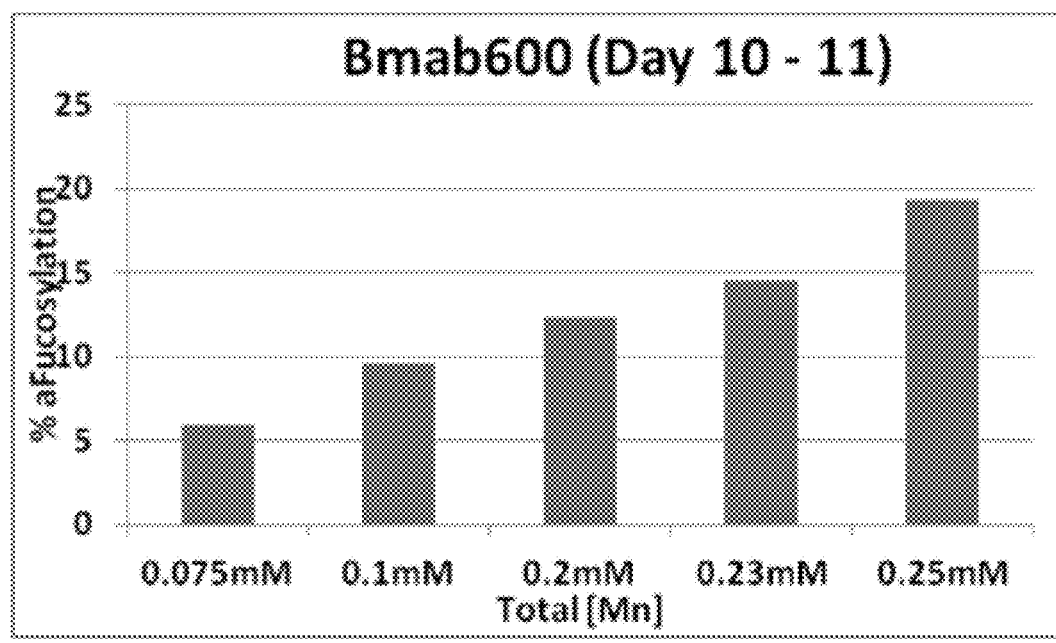
FIG. 11 shows the afucosylation caused by addition of manganese (Mn).

Afucosylation took place as described elsewhere herein (see, e.g., description of FIG. 11). Increased afucosylation of the Fc region of Itolizumab shows a linear increase in the ADCC activity exhibited by the antibody with respect to the positive control antibody (anti-human CD3). This demonstrates the ability of Itolizumab to be more cytotoxic by merely increasing the afucosylated Fc Glycan content. For example, to enhance the ADCC from 20% relative to that of anti CD3 to greater than 40%, the afucosylated content in the antibody should be greater than 10%.

Such increase may be caused by better binding to FcγRIII as shown in the biacore data discussed infra (wherein Bmab 600 binds with better affinity as compared to Tlh). Hence increasing the afucosylated species in the antibody can cause better binding to FcγRIII and this translates into a functional activity of better ADCC.

Figure 7:
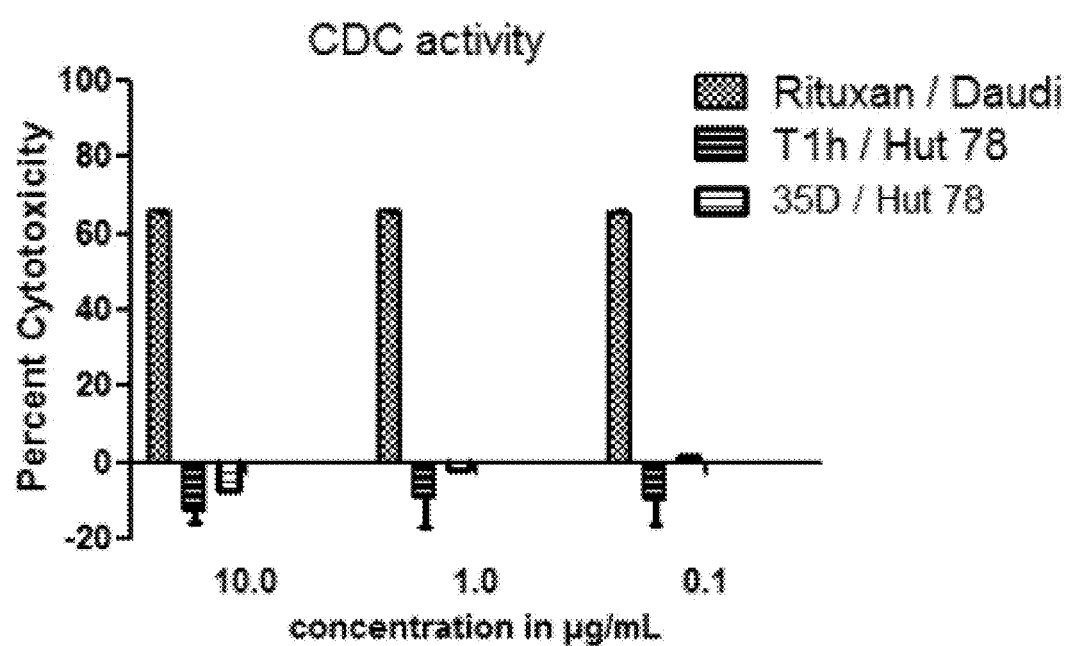
FIG. 7 shows the results of a CDC assay comparing Tlh and Rituximab.

FIG. 7: Results of a CDC assay comparing Tlh and Rituximab

The Human T cell lymphoma cell line Hut 78 (ATCC® TIB-161™), was used to assess the CDC activity of Tlh. $1 \times 10^4$ cells were incubated with the respective drug dilutions at 10 μg/mL, 1 μg/mL and 0.01 g/mL for 20 minutes in a 37° C., 5% $CO_2$ incubator. Pooled normal human serum was added at a final concentration of 1:10 and cells were incubated for 2 hours at 37° C. alamarBlue® (Invitrogen) was added and cells were incubated for 20-22 hours at 37° C. The uptake of the dye by cells, followed by its reduction is read as fluorescence at 530/590 nm.

Rituximab, an anti CD20 targeting CD20 receptors on a B cell line (Daudi) and causing complement-dependent cytotoxicity (CDC) was used as a positive control in the assay to show that the serum components resulting in CDC was intact.

Tlh does not exhibit CDC activity. Increase in the afucosylated species of Itolizumab does not increase the CDC activity of the molecule, concluding that only ADCC effector functions are enhanced with increase in afucosylation.

TABLE 1

Glycan profile of differentially afucosylated Tlh samples used in assays shown in FIGS. 6 and 7.

| Batch | G0-GN | G0f-GN | G0 | G0f | Man5 | G1f-GN, G1 | G1f | Man6, (G1f-GN)S1 |
|---|---|---|---|---|---|---|---|---|
| T1h Range | 0.1-0.5 | 0.8-2.2 | 0.1-0.3 | 23.5-36.7 | 1.2-3.7 | 1.2-3.4 | 37.9-43.8 | 0.6-1.4 |
| 1185/12/03/25D | 0.7 | 2.2 | 5.1 | 45.1 | 3.0 | 3.4 | 31.3 | 1.3 |
| 1185/12/03/27D | 0.5 | 1.5 | 4.3 | 42.7 | 2.6 | 3.6 | 34.4 | 1.3 |
| 1185/12/03/34D | 0.5 | 1.3 | 4 | 45.1 | 6.8 | 2.9 | 29.2 | 1.8 |
| 1185/12/03/31D | 0.6 | 1.5 | 4.5 | 42.4 | 7.3 | 3.7 | 29.1 | 2.1 |
| 1185/11/01/35D | 0.7 | 1.4 | 6.5 | 46.7 | 4.8 | 3.5 | 28.2 | 1.4 |

| Batch | G1FS1, Tri-antennary complex with 1G, hybridS1 | G2f | G2fS1, with small hybrid | G2fS2 | Others hybrid species | Total non fucosylated species |
|---|---|---|---|---|---|---|
| T1h Range | 1.6-2.6 | 8.2-12.2 | 6.5-13.6 | 1.5-3.8 | 0.5-1.3 | 3.95 |
| 1185/12/03/25D | 1.0 | 4.2 | 1.9 | 0.2 | 0.7 | 10.1 |
| 1185/12/03/27D | 1.0 | 5.0 | 2.1 | 0.1 | 0.8 | 8.7 |
| 1185/12/03/34D | 0.9 | 4.2 | 1.9 | 0.7 | 0.9 | 13.1 |

TABLE 1-continued

Glycan profile of differentially afucosylated T1h samples used in assays shown in FIGS. 6 and 7.

| | | | | | |
|---|---|---|---|---|---|
| 1185/12/03/31D | 1.0 | 4.0 | 2.3 | 0.3 | 1.1 | 14.5 |
| 1185/11/01/35D | 0.8 | 3.4 | 1.3 | 0.6 | 0.7 | 13.4 |

The analysis of Glycosylation patterns took place with standard methods. In brief, the antibodies were digested with Peptide-N-Glycosidase F (PNGase F), to deglycosylate the antibodies (see description at FIG. 1 for more details), and the isolated glycanes were collected. The collected glycanes were labeled with anthranicilic acid and then analyzed by means of NP HPLC. Full details of the method are disclosed in Anumula (2012), content of which is incorporated herein by reference.

In this table, the following abbreviations are used: G0=no Galactose, G1=1 terminal Galactose residue, G2=2 terminal Galactose residues, GN=N-Acetyl Glucosamine or GlcNac, F=Fucose, Man5=5 mannose residues, Man6=6 mannose residues and S=Sialic acid.

Figure 15:
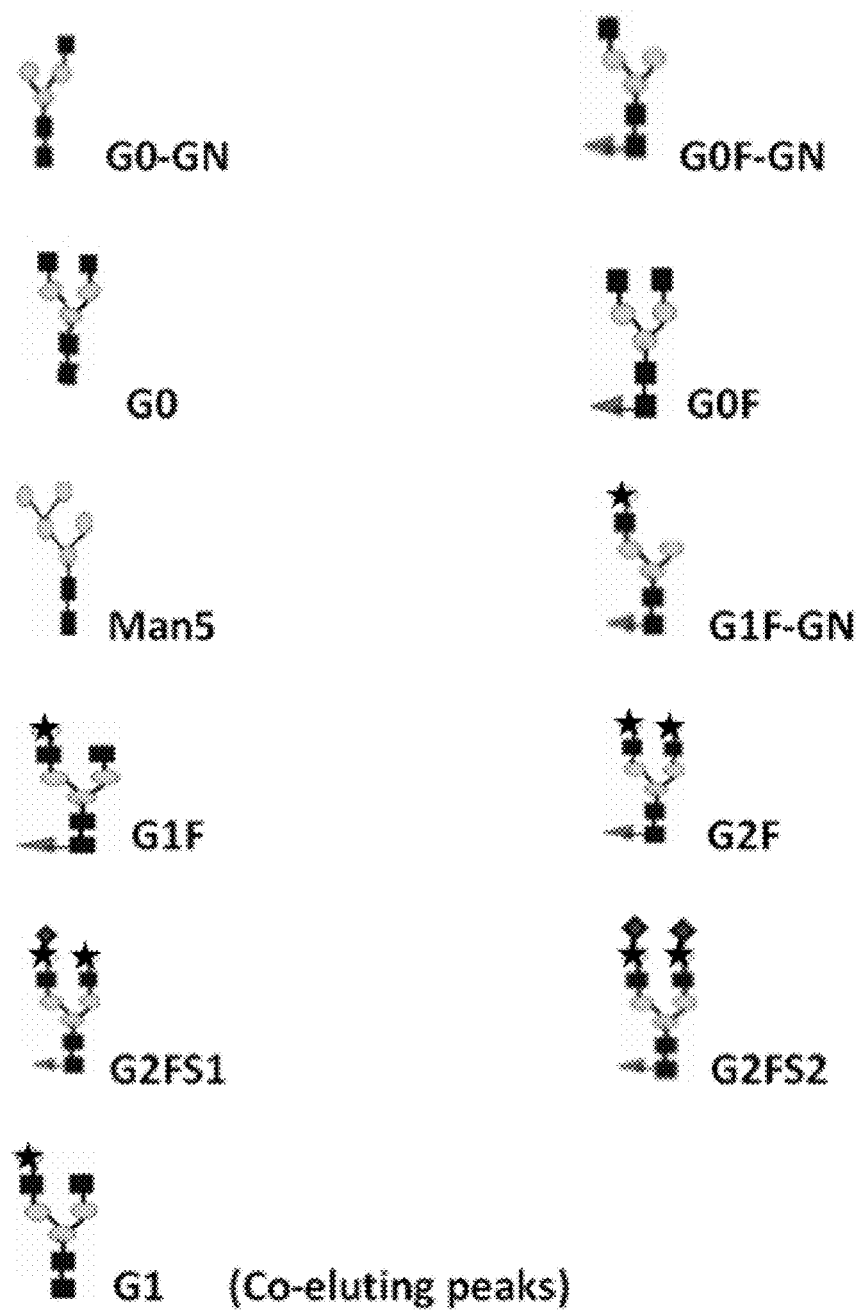
FIG. 15 shows the nomenclature of N-glycan structures.

An explanation of the Glycosylation patterns determined in the course of the experiments shown herein, and the nomenclature used, is provided in FIG. 15.

Figure 8:
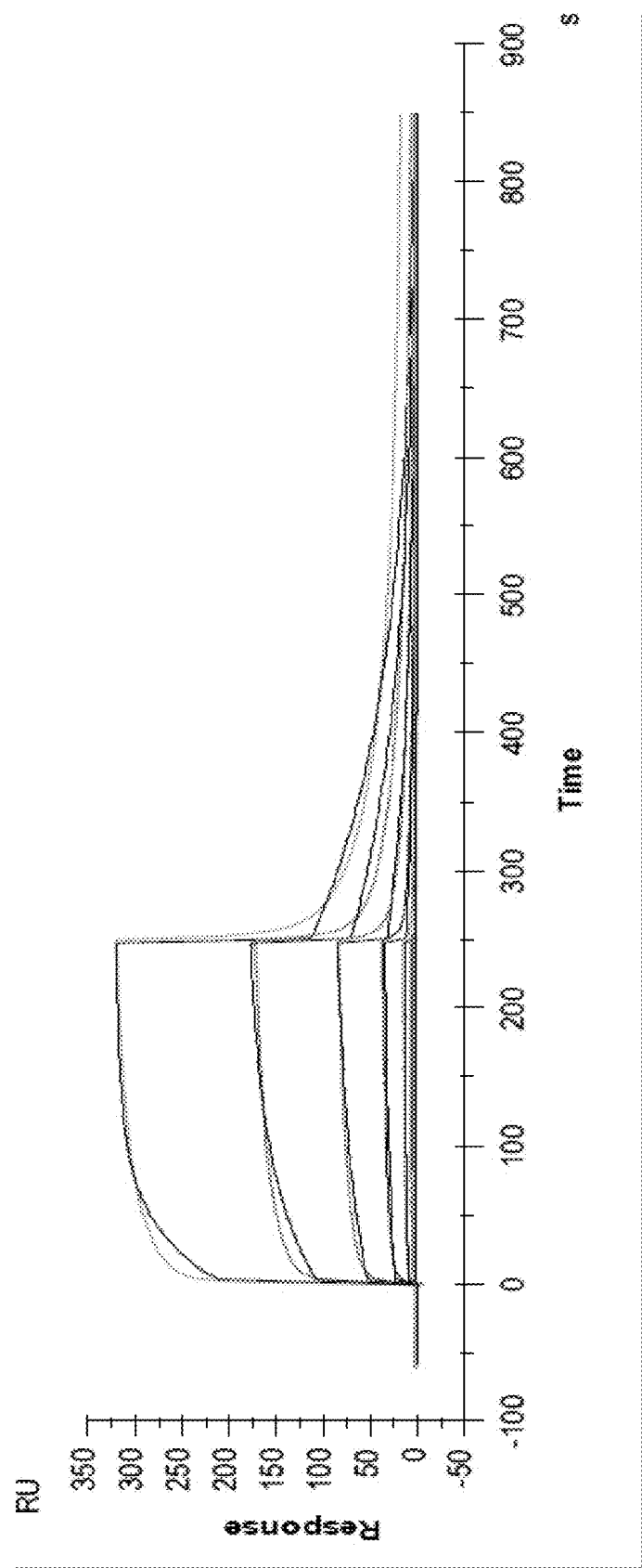
FIG. 8 shows the binding curves of Tlh antibody to FcγRIIIa.
Figure 9:
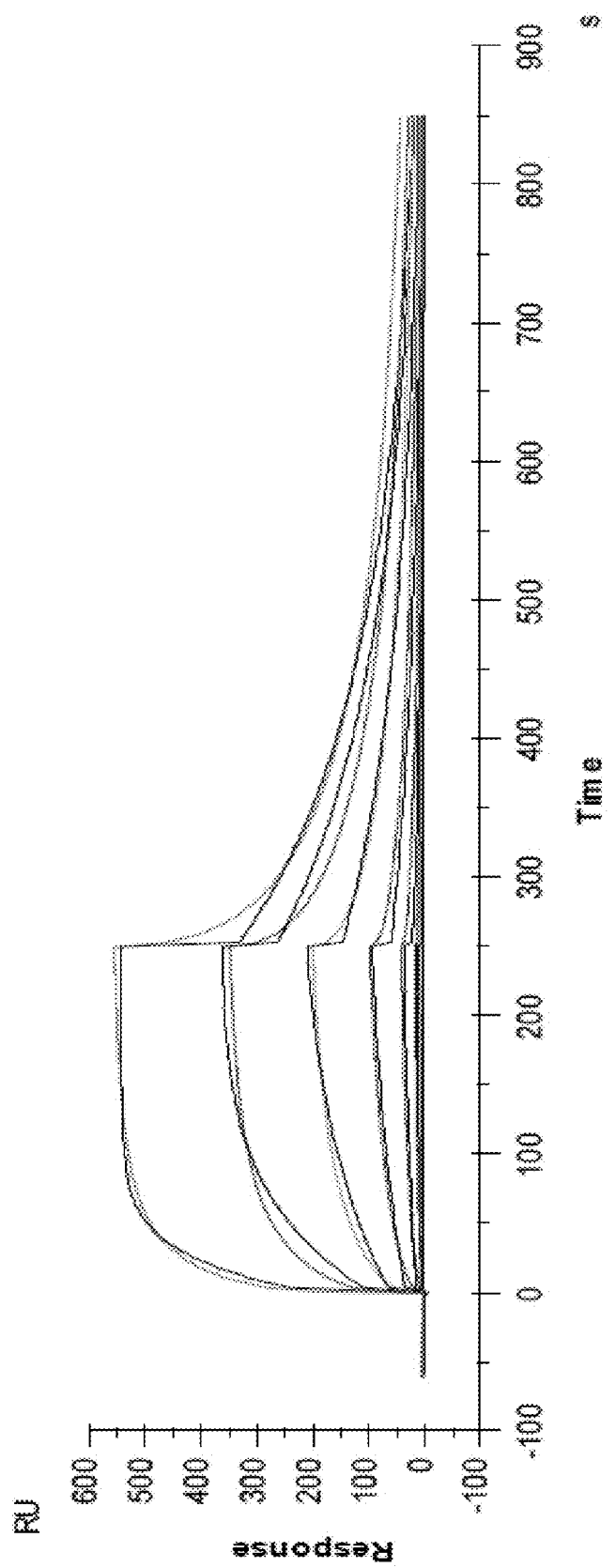
FIG. 9 shows the binding curves of Bmab-600 antibody to FcγRIIIa.
Figure 10:
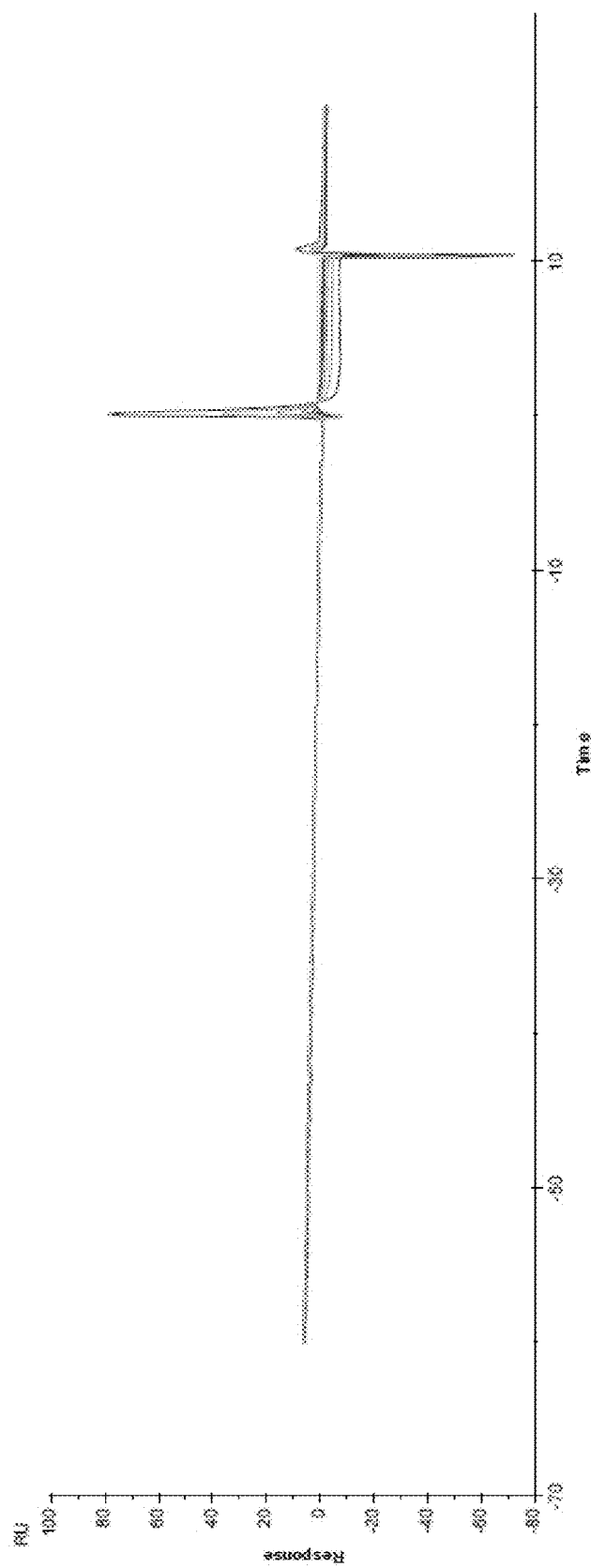
FIG. 10 shows the binding curves of deglycosylated Tlh antibody to FcγRIIIa.

FIGS. 8-10: Binding curves of T1h to FcγRIIIa detect with Plasmon resonance

BIAcore is an analytical device which detects differences in surface plasmon resonance-based changes in the refractive index near a sensor surface. This method of determining affinity constants of an antibody for Fc receptors ligands has been used widely. In order to detect an interaction one molecule (the ligand) is immobilized onto the sensor surface. Its binding partner (the analyte) is injected in aqueous solution (sample buffer) through the flow cell, also under continuous flow. As the analyte binds to the ligand, the accumulation of protein on the surface results in an increase in the refractive index, which is plotted against time to yield a sensorgram. Association ($K_a$), dissociation-rate constants ($K_d$) and equilibrium dissociation constants ($K_D$) are determined from the analysis of sensorgrams.

FcγRIIIa is considered as an intermediate affinity receptor. It can variably bind monomeric IgG and appears to have a high affinity for IgG than the lower affinity Fc gamma receptors. They are expressed on the NK cells and monocytes of the blood cells.

The Fc portions of Bmab-600 and T1h bind to FcγRIIIa with different affinities as the post translational modifications, especially the afucosylation pattern varies with cell line and culture conditions. We evaluated these two products binding affinities towards FcγRIIIa in Biacore instrument. The binding affinity results of Bmab-600 show higher affinity in binding to FcγRIIIa receptors in comparison to T1h. The following samples were analyzed on the surface immobilized with FcγRIIIa receptor:
1. T1h antibody
2. Bmab-600 antibody
3. Deglycosylated T1h antibody.

Each sample was analyzed two times and the average $K_D$ (μM) values are reported and compared against each other. FIG. 8 shows the binding curves of T1h antibody to FcγRIIIa, FIG. 9 shows the binding curves of Bmab-600 antibody to FcγRIIIa, and FIG. 10 shows the binding curves of deglycosylated T1h antibody to FcγRIIIa.

The method was sensitive and was able to pick-up the differences between afucosylation differences that were existing inherently in the differentially afucosylated samples of Bmab-600 and T1h. The data also shows that as the afucosylation levels increases the FcγRIIIa binding affinity values decreases (meaning higher affinity) proportionally. The method specificity was also demonstrated by analyzing the deglycosylated sample of T1h where no binding interactions was observed.

TABLE 2

Kinetic values of T1h antibody to FcγRIIIa (see FIG. 8)

| Samples | ka (1/Ms) | kd (1/s) | $K_D$ (M) | $K_D$ (μM) | Average $K_D$ (μM) |
|---|---|---|---|---|---|
| T1h (NS0) | 1.52E+04 | 5.65E−03 | 3.72E−07 | 0.372 | 0.440 |
| | 1.16E+04 | 5.88E−03 | 5.08E−07 | 0.508 | |

TABLE 3

Rate constant values of Bmab600 antibody to FcγRIIIa (see FIG. 9)

| Samples | ka (1/Ms) | kd (1/s) | $K_D$ (M) | $K_D$ (μM) | Average $K_D$ (μM) |
|---|---|---|---|---|---|
| Bmab-600 (CHO) | 2.46E+04 | 4.76E−03 | 1.93E−07 | 0.193 | 0.200 |
| | 2.78E+04 | 5.73E−03 | 2.07E−07 | 0.207 | |

TABLE 4

Rate constant values of deglycosylated T1h antibody to FcγRIIIa (see FIG. 10)

| Samples | ka (1/Ms) | kd (1/s) | $K_D$ (M) | $K_D$ (μM) | Average $K_D$ (μM) |
|---|---|---|---|---|---|
| T1h (NS0) | Negative interaction | | | | |

TABLE 5

Rate constant values of differentially afucosylated samples of Bmab-600 and T1h antibody to FcγRIIIa (see FIG. 10)

| Samples | % afucosylation | ka (1/Ms) | kd (1/s) | $K_D$ (M) | $K_D$ (μM) |
|---|---|---|---|---|---|
| T1h | 2.5 | 1.18E+04 | 5.54E−03 | 4.686E−07 | 0.468 |
| Bmab-600 | 5.1 | 1.28E+04 | 4.20E−03 | 3.28E−07 | 0.328 |
| Bmab-600 | 9.6 | 1.96E+04 | 6.00E−03 | 3.06E−07 | 0.306 |
| Bmab-600 | 35.6 | 2.73E+04 | 5.34E−03 | 1.95E−07 | 0.195 |

FIG. 11: Afucosylation caused by addition of manganese (Mn).

Addition of Mn at concentrations higher than the media concentration (0.005 μM) was tested for a CHO-S cell line producing T1h monoclonal antibody. The trials were started with initial cell count of 0.8-0.9 million cells/ml. Regular feeding of glucose and amino acids was carried out during the process to meet the nutritional requirement of cells. Periodic samples were taken to check the cell growth, viability and IgG titre profiles. The broths were harvested at the end of the culture and analyzed for glycosylation profiles as described elsewhere herein.

The trials were done in 2 sets. The first set was carried out in shake flasks and the second set was performed in 50 L bioreactors. Manganese was added in culture medium and through feed at specified intervals during the run.

FIG. 11 shows an increase in afucosylation level with addition of Manganese in the culture medium and through feed. The afucosylation profiles correspond to day 10 sample in case of 0.1 mM, 0.2 mM and 0.25 mM; and day 11 in case of 0.075 mM and 0.23 mM. The results are summarized in the following tables:

TABLE 6

Glycan profile of a 10-day shake flask trial with 0.1 mM, 0.2 mM and 0.25 mM Manganese (Mn) concentration

| Mn Concentration tested | G0-GN | G0f-GN | G0 | G0f | Man5 | G1f-GN, G1 | G1f | Man6 (G1f-GN)S1 |
|---|---|---|---|---|---|---|---|---|
| 0.1 mM | 0.5 | 1.1 | 4.9 | 56.7 | 3.1 | 1.9 | 25.2 | 1.1 |
| 0.2 mM | 0.6 | 0.9 | 6.3 | 55.1 | 4.2 | 2.3 | 24.1 | 1.2 |
| 0.25 mM | 1.2 | 1 | 10.3 | 51.2 | 6.8 | 3.1 | 20.3 | 1.1 |

| Mn Concentration tested | G1FS1, Triantennary complex with 1 G, hybrid S1 | G2f | G2fS1, with small hybrid | G2fS2 | Other hybrid species | Afucosylation |
|---|---|---|---|---|---|---|
| 0.1 mM | 0.8 | 2.5 | 1.2 | 0.5 | 0.5 | 9.6 |
| 0.2 mM | 0.8 | 2.4 | 1.1 | 0.5 | 0.7 | 12.3 |
| 0.25 mM | 0.7 | 1.9 | 1 | 0.4 | 1 | 19.4 |

TABLE 7

Glycan profile of 50 L batches run for 11 days with 0.075 mM and 0.23 mM Mn concentrations

| Mn Concentration tested | G0-GN | G0f-GN | G0 | G0f | Man5 | G1f-GN, G1 | G1f | Man6 (G1f-GN)S1 |
|---|---|---|---|---|---|---|---|---|
| 0.075 mM | 0.2 | 1.1 | 2 | 40.6 | 1.9 | 2.3 | 38.9 | 1.8 |
| 0.23 mM | 0.6 | 1.5 | 4.5 | 42.4 | 7.3 | 3.7 | 29.1 | 2.1 |

| Mn Concentration tested | G1FS1, Triantennary complex with 1 G, hybrid S1 | G2f | G2fS1, with small hybrid | G2fS2 | Other hybrid species | Afucosylation |
|---|---|---|---|---|---|---|
| 0.075 mM | 1.1 | 6.2 | 2.3 | 0.9 | 0.8 | 5.9 |
| 0.23 mM | 1 | 4 | 2.3 | 0.3 | 1.1 | 14.5 |

Based on the above experiments, an increase in % afucosylation was observed with increase in total manganese concentration. The cell growth, viability and IgG titre profiles were not affected by Mn addition.

Figure 12:
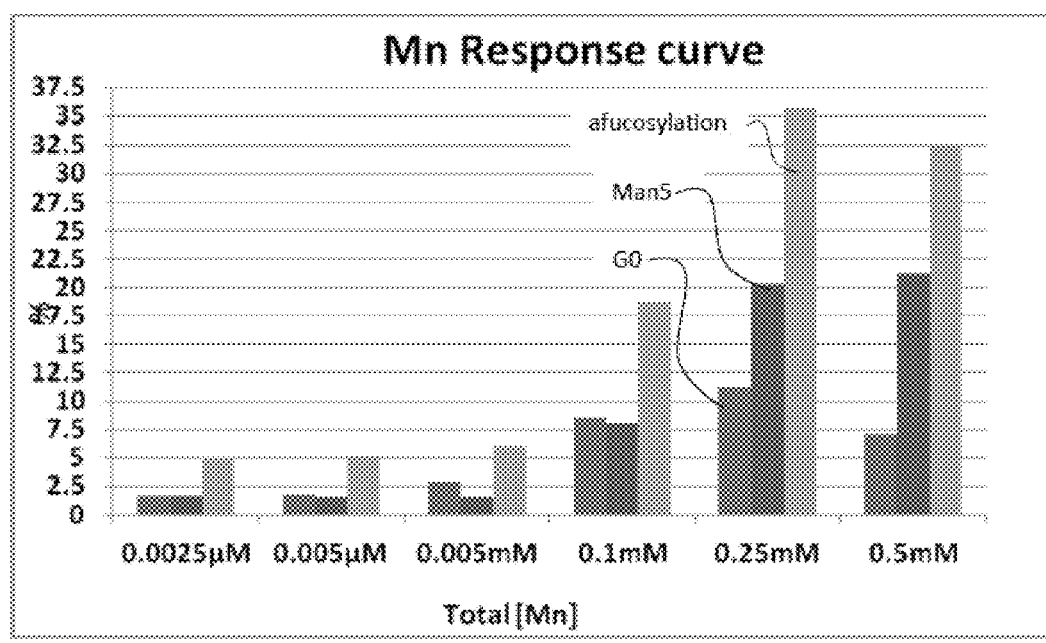
FIG. 12 shows the increase in G0, Man5 and afucosylation levels by addition of manganese (Mn).

FIG. 12: Increase in G0, Man5 and afucosylation levels by addition of manganese (Mn).

The Effect of manganese in the range of 0.0025 μM to 0.5 mM was tested by varying the concentration in culture medium. No manganese addition was done through feeds. The trial was carried out in shake flasks and samples were analyzed for glycosylation profiles on day 8. A gradual increase in G0, Man5 and afucosylation levels with an increase in manganese concentration could be observed.

Figure 13:
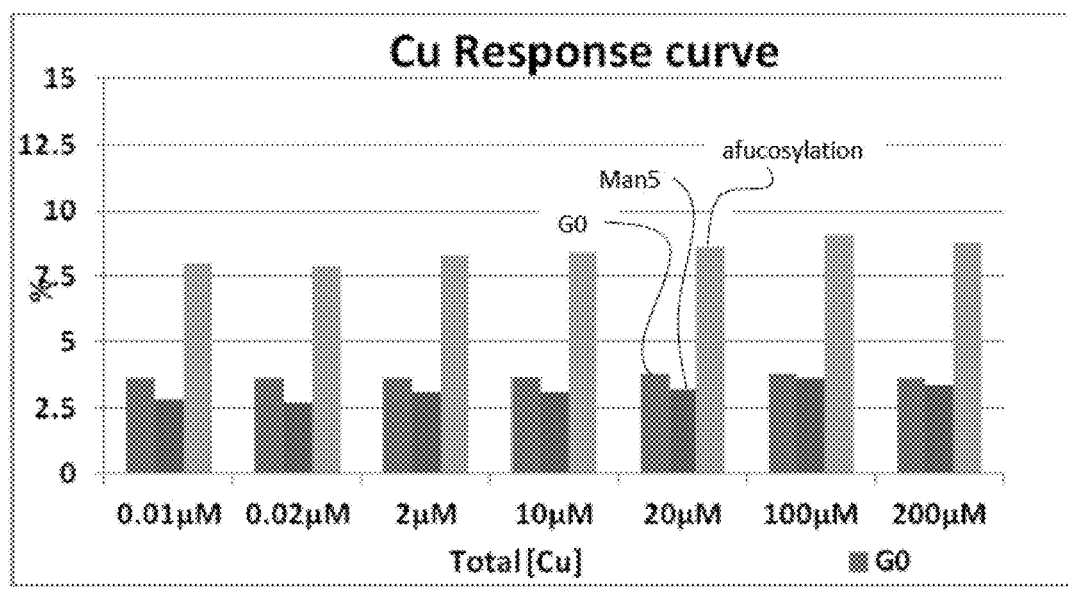
FIG. 13 shows copper concentration does not have an effect on fucosylation.

FIG. 13: Copper concentration does not have an effect on fucosylation.

To evaluate the effect of other divalent cations, Cu was selected for the study since Cu was also a co-factor in the glycosylation pathway (for enzyme Sialyltransferase). Different concentrations of copper in culture medium in the range of 0.01 μM to 200 μM were tested in shake flasks. No increase/effect in any of the values (G0, Man5 and afucosylation) was observed, as shown in FIG. 3. This establishes that copper ions does not affect afucosylation levels in proteins.

Figure 14:
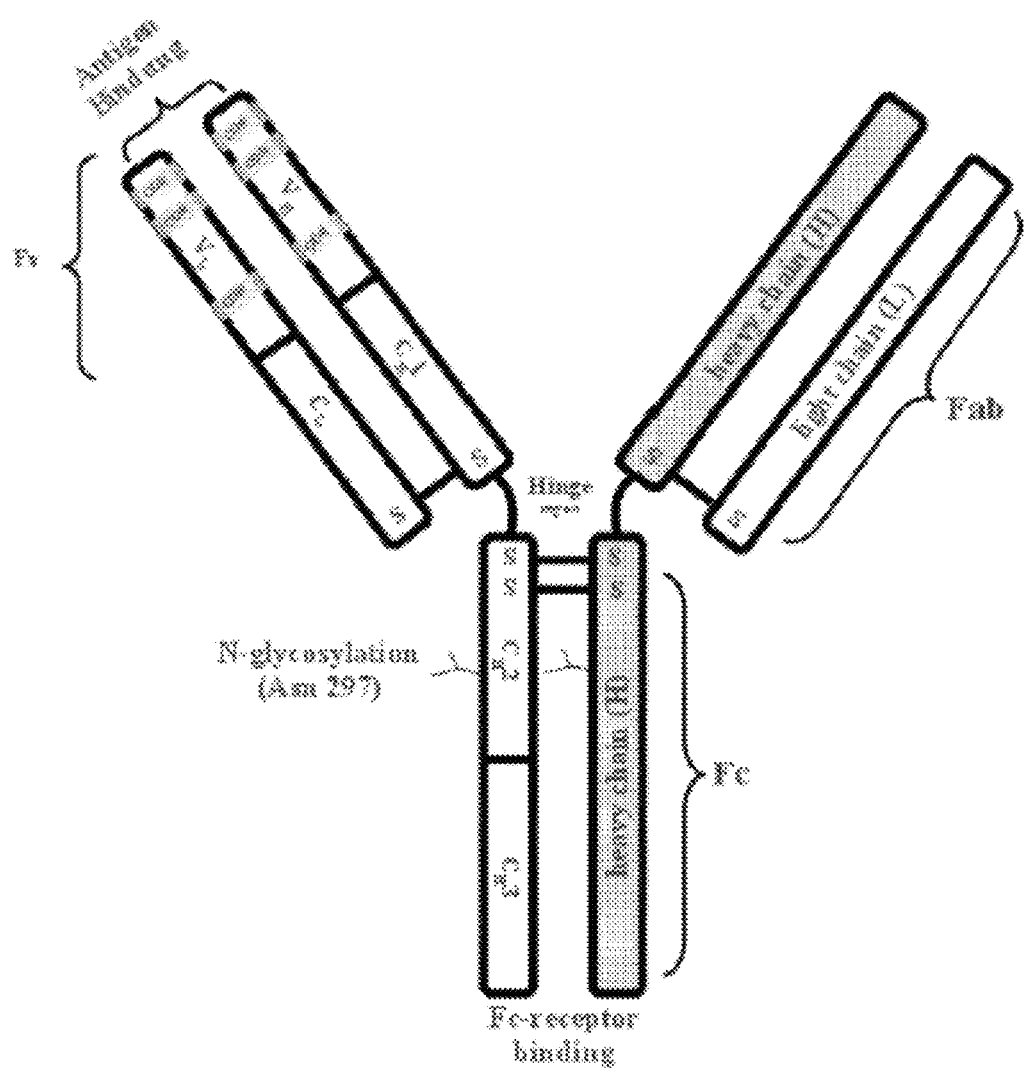
FIG. 14 shows a schematic representation of an immunoglobulin G.

FIG. 14: Schematic representation of an immunoglobulin G.

FIG. 14 shows a schematic representation of an immunoglobulin G (IgG). An IgG is composed of two identical light chains (each composed of two domains, $V_L$ and $V_H$) and two identical heavy chains (each composed of four domains, $V_H$, $C_H 1$, $C_H 2$ and $C_H 3$). Antigen binding surface is formed by the variable domains of heavy and light chains and the effector function, such as complement activation and binding of cytotoxic cells is mediated by the Vc region of the antibody.

FIG. 15: Nomenclature of N-glycan structures.

FIG. 15 shows an overview of different N-glycans. Generally, the term "N-glycosylation" refers to glycosylation of the amino acid residue asparagine (N). Here, an oligosaccharide chain is attached by oligosaccharyltransferase to those asparagine residues which occur in the tripeptide sequences Asn-X-Ser or Asn-X-Thr, where X can be any amino acid except Pro.

The experiments shown herein clearly demonstrate that a) the fucose content of glycoproteins can be manipulated by varying the total concentration of manganese or manganese ions in media and feeds in the protein expression process b) increasing total concentration of manganese or manganese ions leads to an increased afucosylation, or to a decreased fucose content in the glycosylation pattern of glycoproteins.
c) in immunoligands like antibodies having an Fc region, protein expression in the presence of an elevated concentration of manganese or manganese ions leads to (i) a higher degree of afucosylation and (ii) an increased ADCC
d) in these immunoligands, increasing the degree of afucosylation does not lead to an increased CDC
e) deglycosylation of immunoligands like antibodies having an Fc region, by contrast, does not lead to an increased ADCC
f) other than afucosylation, deglycosylation of immunoligands like antibodies having an Fc region can lead to loss of functional activity of such immunoligands, in particular if such functional activity is related with activity like effector function and/or ADCC.

REFERENCES

Jayaraman K, Nature Biotechnology 31, 1062-1063 (2013)
Anumula KR, Glycobiology (2012) 22 (7): 912-917.
Shields et al, J Biol Chem 277:26733-26740.
Konno et al, Cytotechnology. 2012 May; 64(3):249-65
Aruffo et al, J. Exp. Med. 1991, 174:949.
Kantoun et al, J. Immunol. 1981, 127:987.
Mayer et al., J. Neuroimmunol. 1990. 29: 193.
Matsumoto, et al., J. Exp. Med. 1991, 173:55.
Resnick et al, Trends Biochem. Sci. 1994, 19:5.
Jones et al, Nature. 1986, 323:346.
Friedman et al. 1993, PNAS 90:6815.
Goldberger, et al, J. Biol. Chem. 1987, 262: 10065 Wijingaard et al, J. Immunol. 1992, 149:3273 Law et al., Eur J. Immunol. 1993, 23:2320.

That which is claimed is:

1. A method for decreasing fucosylation and increasing Mannose 5 and $GlcNAc_2Man_3GlcNAc_2$ (G0) in the glycosylation pattern of an expressed antibody in an eukaryotic protein expression system, the method comprising:

providing a culturing medium;
introducing into the culturing medium the eukaryotic protein expression system, wherein the eukaryotic protein expression system comprises an expression cassette encoding the expressed antibody, wherein the expressed antibody is Itolizumab, wherein the eukaryotic protein expression system comprises mammalian cells, wherein the mammalian cells are CHO hamster cells;
adding manganese or manganese ions into the culture medium to form a manganese containing culture medium, wherein the manganese or manganese ions is in a concentration range of $\geq 0.075$ mM-$\leq 0.5$ mM;
culturing the eukaryotic protein expression system in the manganese containing medium to obtain the expressed antibody; and
recovering the expressed antibody from the manganese containing medium, wherein the expressed antibody exhibits decreased fucose and increased levels of Mannose 5 and $GlcNAc_2Man_3GlcNAc_2$ (G0) in the glycosylation pattern compared to an expressed antibody cultured in a medium wherein no manganese or manganese ions were introduced into the culture medium.

2. The method according to claim 1, wherein the antibody expressed in claim 1 demonstrates an increased ADCC activity compared to an antibody expressed in the absence of the manganese or manganese ions added to the culture medium.

3. The method according to claim 1, wherein the antibody expressed in claim 1 binds to one or more cellular surface antigen involved in cell-mediated immune defense.

4. The method according to claim 1, further comprising introducing amino acids to the culturing medium to maintain cell growth and expression of the antibody expressed in claim 1.

5. The method according to claim 1, wherein the manganese or manganese ions are in a concentration range of $\geq 0.1$ mM-$\leq 0.25$ mM.

* * * * *